United States Patent
Pettibon

(10) Patent No.: US 6,788,968 B2
(45) Date of Patent: Sep. 7, 2004

(54) SYSTEM FOR SPINAL AND POSTURE EXAMINATION AND TREATMENT

(76) Inventor: Burl Pettibon, 89 Raft Island Dr., Gig Harbor, WA (US) 98335

(*) Notice: Subject to any disclaimer, the term of this patent is extended or adjusted under 35 U.S.C. 154(b) by 207 days.

(21) Appl. No.: 09/978,748

(22) Filed: Oct. 16, 2001

(65) Prior Publication Data

US 2002/0169376 A1 Nov. 14, 2002

Related U.S. Application Data

(63) Continuation-in-part of application No. 09/855,998, filed on May 14, 2001, now abandoned.

(51) Int. Cl.[7] .................................................. A61B 5/05
(52) U.S. Cl. ..................................................... 600/427
(58) Field of Search ................................ 600/407–471, 600/594, 595; 601/127, 2; 602/32–40, 16–18; 128/898; 2/171

(56) References Cited

U.S. PATENT DOCUMENTS

| | | | | |
|---|---|---|---|---|
| 2,701,564 A | * | 2/1955 | Wilhelm | ...................... 602/32 |
| 4,716,891 A | * | 1/1988 | Yorgan | ...................... 601/127 |
| 5,088,504 A | * | 2/1992 | Benesh et al. | ............... 600/594 |
| 5,569,175 A | * | 10/1996 | Chitwood | ..................... 602/32 |
| 5,582,186 A | * | 12/1996 | Wiegand | ..................... 600/595 |
| 6,368,292 B1 | * | 4/2002 | Ogden et al. | .................. 601/2 |
| 6,517,506 B1 | * | 2/2003 | Pettibon | ...................... 602/32 |

* cited by examiner

*Primary Examiner*—Ali Imam
(74) *Attorney, Agent, or Firm*—Seed IP Law Group PLLC

(57) ABSTRACT

A method is provided for spinal examination and treatment that includes obtaining a first image of one or more areas of a patient's skeletal system; determining areas of abnormal condition of the patient's skeletal system; weighting the patient's skeletal system to correct the areas of abnormal condition; and obtaining further images of the patient's skeletal system, redetermining the presence of areas of abnormal condition of the patient's skeletal system, and adjusting the weighting of the patient's skeletal system until a final weighting is reached where the patient's areas of abnormal condition of the skeletal system are no longer abnormal. Ideally, weighting the patient's skeletal system includes attaching at least one weight externally to the patient's body with at least one removable external weight holder. The patient's body should remain weighted with a final weight for at least two to three times daily for a predetermined period of time to achieve the natural spinal alignment and a reduction or elimination of pain due to subluxations in the patient's skeletal system.

28 Claims, 17 Drawing Sheets

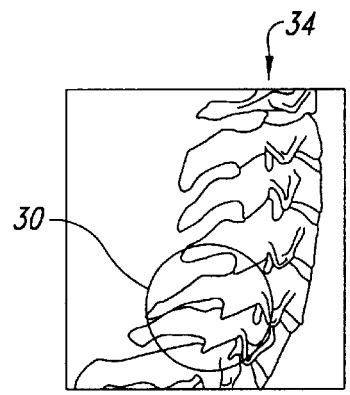
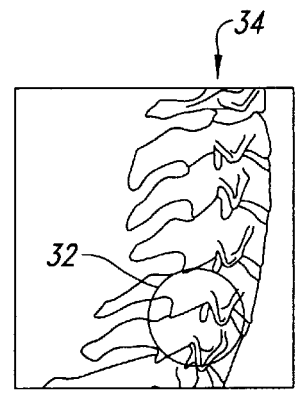
*Fig. 5A*  *Fig. 5B*
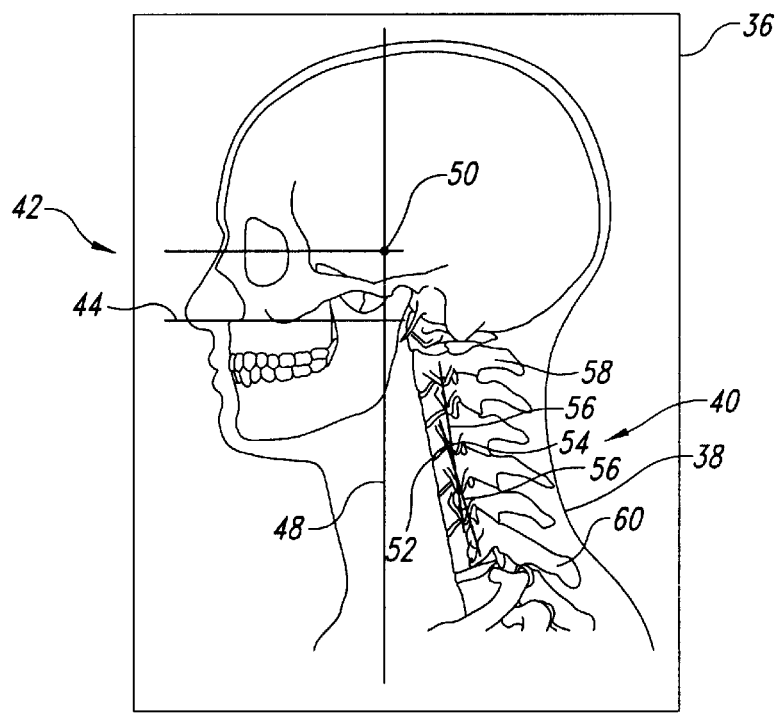
*Fig. 6*

Posture #1: Head level, shoulder high.

Posture #2: Shoulders level, eyes tilted.

Posture #3: Eyes and shoulder level, head lateral shift.

Posture #4: Eyes and shoulder level, head lateral shift.

SYSTEM FOR SPINAL AND POSTURE EXAMINATION AND TREATMENT

CROSS-REFERENCE TO RELATED APPLICATIONS

This application is a Continuation-In-Part of U.S. patent application Ser. No. 09/855,998, filed May 14, 2001, Now Abandoned.

BACKGROUND OF THE INVENTION

1. Field of the Invention

The present invention pertains to musculoskeletal examination, evaluation, and treatment methodology, and, more particularly, to a spinal diagnosis and weighting system that loads the spine in a manner to evoke the body's righting reflexes as an adjusting procedure for spinal correction, rehabilitation, and maintenance.

2. Description of the Related Art

The global human spine is divided functionally into six units, the skull, the cervical region (C1 to C4), the thoracic region (C5 to T7), the lower thoracic region (T8 to L2), the lumbar region, (L1 to L5), and the sacral region (S1 to S5, which are fused together). The neck, or cervical spine, has seven vertebrae that assume a natural anterior convex curvature, known as lordosis.

With correct lateral spine posture, there is forward lordotic curve in the cervical region, a backward kyphotic curve in the thoracic region, and a forward lordotic curve in the lumbar region. An abnormal posture with an exaggerated backward curvature of the spine in any region is called kyphosis and resembles a hunch-back posture. A third abnormal posture, scoliosis, is evidenced by an S-shaped curvature of the spine when viewed from the back.

The spine may be divided further into single functional units that consist of a single vertebrae and the disc that separates them. The anterior portion of the vertebral functional unit is the weight bearing portion, and it is ideally constructed with two rounded vertebrae with flattened ends. These vertebrae are separated by an invertebral disc that acts as a spacer and shock absorber.

A natural alignment or neutral spine is characterized as a mid-way point between maximum anterior pelvic tilt and a maximum posterior pelvic tilt. This should be a comfortable position with the shoulders held back and relaxed and the head situated straight ahead with the hard palate parallel to the floor. If a plumb line were dropped from the center point of the head to the floor, this line would go through specific points of spinal joints at each level. More specifically, with normal lordosis, the line would pass through the anterior third of the C4/C5 disc, and back of the center of the body of the L-3 vertebrae. For the best function and durability of the spine, it is important to maintain proper lordosis in an effort to allow weight bearing to be done by the parts of the spine that are designed to handle it.

Normal alignment, curvature, and pelvic angle are important to minimize back and other joint problems. When injuries occur, the neck and other joints can assume an altered position and posture, sometimes referred to as subluxation. This condition results when there is an incomplete dislocation of a joint. Although a relationship between the joint members is altered, contact between joints surfaces remain. When neutral alignment is not maintained, there is an increase in the likelihood of injury, promotion of wear and tear of the joints, and a slowing down of the recoverability. Hence, proper posture and alignment and full range of motion are mandatory for normal spinal integrity.

Loss of neutral alignment can result in a number of maladies, including loss of the ability of the skull to forward flex on the atlas, which produces a forward head posture. Forward head posture generally causes a loss of the cervical lordotic curve. Weakened or injured muscles and ligaments can result in a high shoulder which is commonly associated with a lateral acute angle deviation to the high shoulder side that forms the lower cervical and upper dorsal spine (C-D) angle on that side. An associated subluxation is forward protruding hip posture.

SUMMARY OF THE INVENTION

The present invention is directed to a system for musculoskeletal examination, evaluation, and treatment that loads the spine in a manner to evoke and reprogram the body's righting reflexes and involved muscles, which in turn results in spinal and postural correction, rehabilitation, and maintenance. In accordance with one embodiment of the invention, a method for spinal and postural examination and treatment is provided that includes obtaining a first x-ray image of a patient's cervical spine and head, determining the head position and the lordotic curvature of the cervical spine, then weighting the patient's head, and obtaining further x-ray and images of the patient's cervical and spine and head with subsequent remeasuring of the head's position and the lordotic curvature and adjusting the weighting of the patient's head as needed to obtain a final weight that will normalize the alignment of the spine. Ideally the final weighting is reached where the center of the patient's head is substantially aligned in the lateral x-ray over the anterior one third of the C4/C5 disc.

In accordance with another aspect of the invention, weighting of the patient's head comprises attaching one or more weights to the front or side of the patient's head with an external removal weight holder. Ideally, weighting of the patient's head with the final weight occurs daily for a predetermined period of time, and at least two to three times daily for the predetermined period of time.

In accordance with another aspect of the invention, adjusting the weight on the patient's head comprises adjusting one or more of either the location, position, or the amount of the weight on the patient's head.

In accordance with another embodiment of the invention, a method for spinal examination and treatment is provided that includes obtaining a first image of a patient's spine, determining if the spine is compensated by a low shoulder, weighting the low shoulder of the patient, and obtaining further images of the patient's spine with subsequent determination of spinal compensation and adjusting the weighting of the patient's shoulder repeatedly until the spine is substantially in alignment with itself.

In accordance with a further embodiment of the invention, a method for spinal examination and treatment is provided that includes obtaining a first image of a patient's pelvic and lower lumbar area, determining if the patient's hip is rotated forward, weighting the patient's hip, and obtaining further images of the patient's pelvic and lower lumbar area with subsequent redetermining if the patient's hip is rotated forward and adjusting the weighting on the patient's hip until a final weighting is reached where the hip is no longer rotated forward.

In accordance with yet a further embodiment of the invention, a method for examining and treating a patient's skeletal system is provided that includes obtaining a first image of one or more areas of a patient's skeletal system; determining areas of abnormal condition of the patient's skeletal systems; weighting the patient's skeletal system; and obtaining further images of the patient's skeletal system with subsequent redetermining the presence of areas of abnormal condition and adjusting the weight of the patient's skeletal system until a final weighting is reached where the patient's areas of abnormal condition are no longer abnormal. Ideally, the weighting of the patient's skeletal system comprises attaching at least one weight externally to the patient's body with at least one removal external weight holder.

BRIEF DESCRIPTION OF THE DRAWINGS

The following detailed description of representative embodiments of the system of the present invention will be more readily appreciated as the same become better understood from the accompanying drawings, wherein;

FIGS. 5a and 5b are x-rays of a portion of the spine showing joint injury;

FIG. 6 is an x-ray of the neck and spine showing stress lines and measurement of vertebrae position relative to the skull;

DETAILED DESCRIPTION OF THE INVENTION

The system and methodology of the present invention will now be described in conjunction with FIGS. 1–18, which system is also known as the PETTIBON WEIGHTING SYSTEM. This system has been developed utilizing the principles of neuro-physiology involved in the body's righting reflexes.

More particularly, the righting reflexes maintain the top side of the body in an uppermost orientation. That is, there are five righting reflexes for the body and head that maintain the spine and other elements of the musculoskeletal system in neutral alignment. These are as follows:

(1) The labyrinthine righting reflex that maintains the head's orientation in space (mid-brain);

(2) The body righting reflex that keeps the head oriented to the body (mid-brain);

(3) The body righting reflex from the body surface receptors that orient the body in space (mid-brain);

(4) The neck righting reflex that keeps the body oriented to the head (medulla);

(5) The optic righting reflex that keeps the head in proper orientation (optic cortex).

Figure 1:
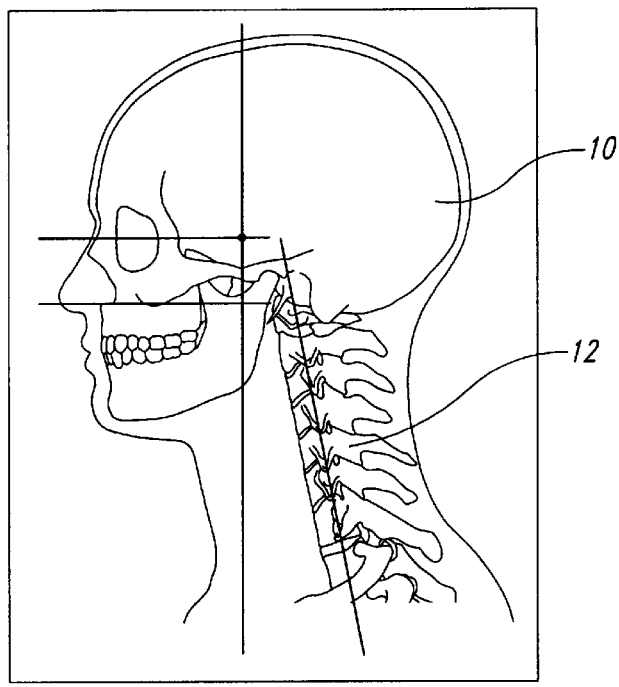
FIG. 1 is an x-ray of the head and neck showing forward head posture.

Loss of the ability of the skull 10 to forward flex on the atlas generally produces a forward head posture, as shown in FIG. 1. This forward head posture almost always causes a loss of the cervical lordotic curve on the spine 12. In experiments on patients having this condition, S-EMG and x-ray techniques were used to evaluate the effect of weight placed on the back of the patient's head. This posterior head weighting caused the S-EMG reading to equalize; but it also caused exacerbation of the forward head posture, and further loss of the cervical curve was produced.

Figure 2:
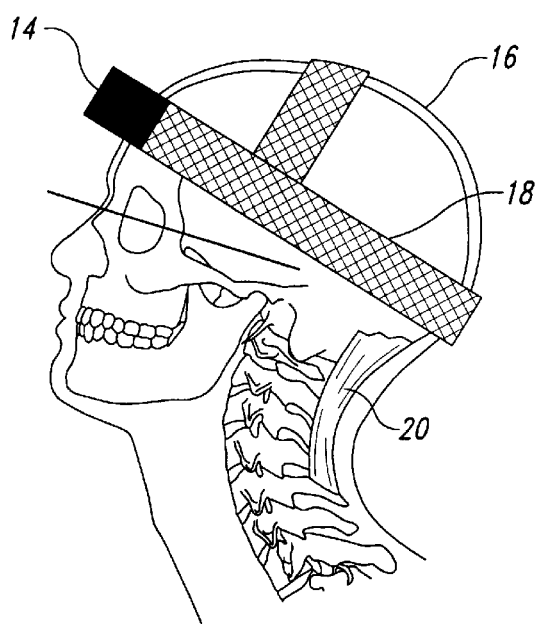
FIG. 2 is a side view of the head and neck illustrating forward head posture rotated upward into extension.

In accordance with the present invention, a frontal head weight 14 placed externally on the head 16 with a removable weight holder 18 produced an equal S-EMG reading but a positive positional reactive response. In other words, the frontal head weighting caused contraction of the cervical extensor muscles 20, which in turn caused the patient's forward head posture to be rotated upward into extension, as shown in FIG. 2.

Figure 3:
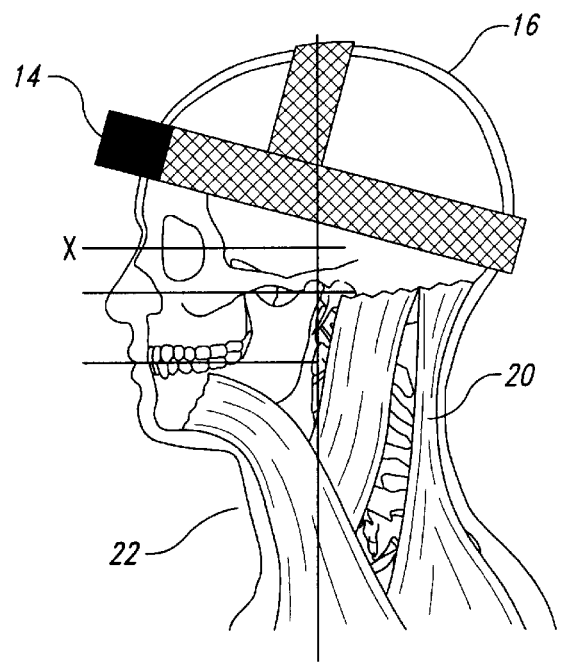
FIG. 3 illustrates activation of optic, labyrinthine, and cervical joint receptor righting reflexes, including involved muscles.
Figure 4:
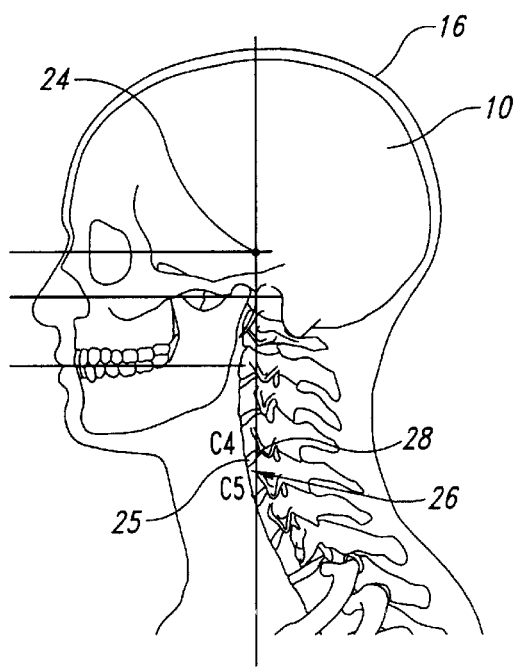
FIG. 4 is an illustration of the head and neck showing the center of the skull normalized over the front of the C4/C5 disc.

However, when the head 16 is rotated upward into extension from the horizontal plane X, the optic, labyrinthine, and cervical joint receptor righting reflexes are activated, which in turn cause the cervical flexor muscles 22, including the muscles of mastication, to contract, as shown more clearly in FIG. 3. Contraction of the cervical flexor muscles 22 rotate the front of the head back down until the skull and eyes are again horizontal and perpendicular to gravity.

However, the action required to rotate the head 16 back down perpendicular to gravity is opposed by the extensor muscles. X-rays show that the front of the head 16 is not allowed to be rotated back down so that it and the eyes are perpendicular to gravity without also forcing the head 16 to move backwards until the center 24 of the skull 10 (front of the sella turcica) is normalized over the front 25 of the C4/C5 disc 28. In this condition, the cervical flexor 22 and extensor muscles 20 are now working in concert under the direction and control of the nervous system and its righting reflexes to correct forward head posture and cervical lordosis. As shown more clearly in FIG. 3, cervical lordosis is reestablished when the cervical flexor 22 and extensor muscles 20 equalize and are strong enough to correct it. Once this is achieved, the S-EMG will equalize. This strengthening and equalization is time dependent with the actual time varying with each patient.

After the cervical spine alignment (head posture and lordosis) has begun to be reestablished, lower spine form and function is also reestablished. Neural impedance is cleared, and pain elimination follows.

The procedures for weighting x-ray evaluation and examination to identify joint and ligament instability and to determine the needs of the patient will now be described. The weight necessary to produce the desired result will vary from patient to patient. Some may require very small amounts of frontal head weighting in order to cause the center of the skull mass 10 (front of the sella turcica) to be aligned over the anterior one third 26 of the C4/C5 disc 28 and the cervical lordosis to be reestablished, while others may require larger amounts of weight.

The Pettibon Spine Weighting System thus begins with head and shoulder weighting (shoulder weighting and amounts are described later). When used correctly, the following procedures balance muscles while restoring their strength and endurance. This system is extremely effective when used in both the clinic and at home. When used in tandem, the clinic and home procedures form an adjusting mechanism for spinal correction, rehabilitation, and maintenance of the normal lateral cervical spine.

The frontal head weighting is utilized for skull-atlas non forward flexion and over extension correction, forward head posture correction, and cervical lordosis correction. It should be noted that frontal head weighting often identifies joint injury 30 and ligament instability 32 of the spine 34 that was not evident on non-weighted neutral lateral or motion x-rays, as shown in FIGS. 5a and 5b, respectively. Also, when frontal head weighting causes the joint to abnormally separate, the amount of weight should be reduced until the abnormal weight resumes its original appearance seen on the neutral lateral x-ray. The joint should then be reexamined in one to three weeks. To reexamine, the amount of weight that caused the joint separation should be added and an x-ray retaken.

To assess the amount of weight needed for each patient, the following procedure should be undertaken.

Firstly, a neutral lateral cervical x-ray 36 is taken of the patient's neck 38 and spine 40. Preferably, the x-ray 36 should be taken on a 10×12 film. The face 42 should be visible on the film so that a hard palette line 44 can be drawn for accuracy.

Secondly, the accurate hard palette line 44 should be erected or drawn on the x-ray 36. For the head position to be accurate, the hard palette line 44 should be 90 degrees plus or minus 2 degrees to the edge of the film, as shown in FIG. 6.

Thirdly, a gravity line 48 should be erected. This line is 90 degrees to the hard palette line 44 and it should intercept the front of the sella turcica above and extend to the bottom of the film below, as also shown on FIG. 6.

Fourthly, the distance of the center of the head 50 should be measured (with the gravity line 48) forward of the front 52 of the C4/C5 disc 54. This measurement should be recorded. In other words, the distance from the front 52 of the C4/C5 disc 54 to the center line or gravity line 48 drawn from the center of the head 50 is to be determined.

Fifthly, Jackson's stress lines 56 should be erected on the back of the C2 and C7 vertebrae 58, 60 and these lines extended until they intersect. The acute angle of these intersected lines should be measured and recorded, including noting the vertebrae where these two lines intersect, as also shown in FIG. 6.

Figure 7:
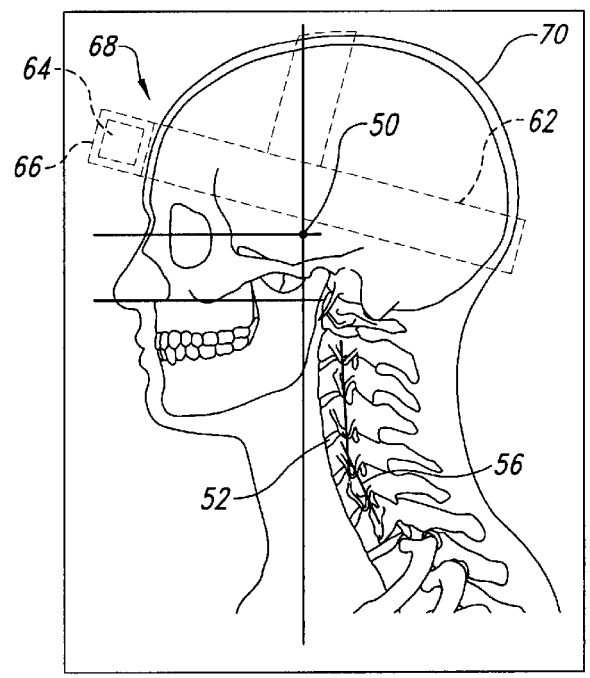
FIG. 7 is an x-ray of the neck and spine with the head weighted in accordance with the present invention.
Figure 8:
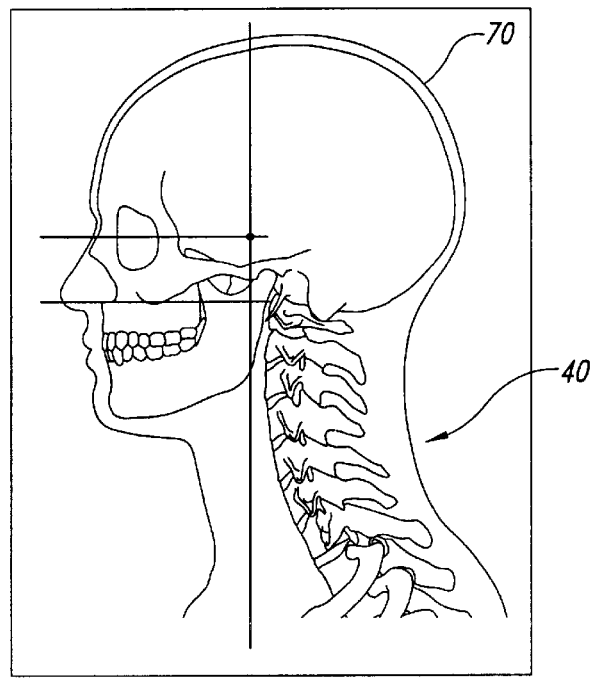
FIG. 8 is an x-ray of the head and neck with the head weighted in accordance with the present invention.

Next, using a large weighted headband 62, three to four pounds of weight 64 should be loaded into a front pocket 66 of the headband 62 and placed on the front 68 of the patient's head 70. With the front 68 of the head 70 now weighted, further x-rays or images should be taken and remeasured in accordance with the procedure outlined above. On the loaded x-ray image shown in FIG. 7, the center 50 of the patient's head 70 should have moved backward, closer to being over the front 52 of the C4/C5 disc 54. The lordotic curve may have been corrected as this point, as shown in FIGS. 7 and 8.

Figure 9:
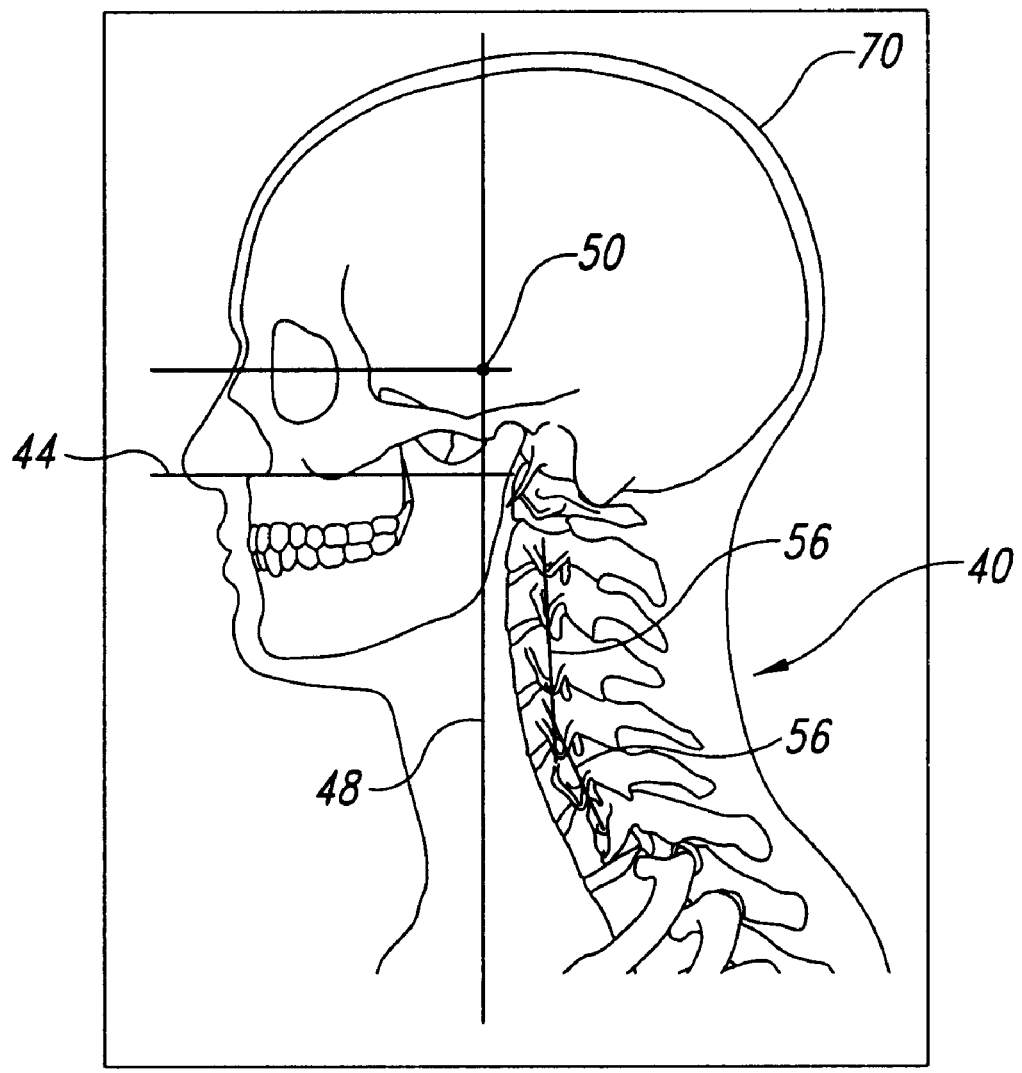
FIG. 9 is an x-ray of the head and neck showing the head weighted with the correct amount of weight to correct the cervical lordosis.

In the event the center 50 of the patient's head 70 is not near or over the front 52 of the C4/C5 disc 54 and if the lordotic curve has not been corrected, additional weight should be added (usually two to three pounds) and additional x-ray images taken and measured repeatedly until the center 50 of the skull is near or over the front 52 of the C4/C5 disc 54. In this way, the amount of weight needed to correct the patient's head posture and to correct the cervical lordosis as shown in FIG. 9 may be determined.

It should be noted that often the lordotic curvature does not correct during the evaluation procedure. However, recentering the skull mass (front of the sella turcica) over the C4/C5 disc is the most important aspect of this procedure. In addition to correcting forward head posture, the procedure in accordance with the present invention forces the involved muscles to begin and to eventually correct the lordosis.

The three conditions to be corrected, as listed above, may be accomplished in as little as a few minutes or they may take up to three months or more. For maximum results, after the proper amount of frontal head weight has been established, the patient should be instructed to wear the frontal head weight while they are in an upright position for at least 20 minutes at a time. Ideally, the patient should commit to doing the exercises twice a day for a period of ninety days, beginning the first thing in the morning after rising in order to equalize the cervical flexors and extensors, as well as to increase strength and endurance so that the correction of spinal form and function is complete and permanent. After the ninety day correction-rehabilitation care is complete, the patient will be able to maintain muscle strength and endurance and the cervical lordosis corrections with one weekly, full-weighted twenty minute exercise session.

Because of weak muscles or recent injuries, some patients do not initially toleration the additional weight. Generally, the most common weight for the introductory period is two to six pounds, with more weight being added at the patient's toleration, until the total reaches the weight necessary to correct the condition. Should the patient not tolerate the initial weight, the length of time the patient is required to wear the initial weight should be increased so that the time-weight ratio is maintained and a lower weight can be used. For example, if the x-ray examination determined that six pounds is required to correct the forward head posture and the patient can only tolerate two pounds, then the patient should wear the two pound weight for sixty minutes. The clinician may expect the same spinal correction when the time is lengthened to compensate for the patient's inability to tolerate more weight.

It should be noted that too much weight will over weight the head, causing the head to rotate forward rather than backward. When this occurs, the patient should be started with lighter weights and have them worn for longer periods of time, as discussed above. The lighter weight may be worn for up to one hour at a time. For the patient that begins with lighter weight, the amount of weight should be increased approximately every other day.

It should further be noted that head weighting should be performed twice daily beginning first thing after rising to follow with cervical traction each morning. Head weighting may cause nausea if it is done later in the day without utilizing the head weighting in the morning.

Also, it has been found that grossly obese patients must distort their body posture backward and their head posture forward in order to sit and to stand. Therefore, frontal head weighting will not work on these grossly obese patients. Attempts to use the procedures may result in dizziness or nausea or other reflex disturbances. The patient should be told that their spine can never be corrected until they shed this excess weight.

Once frontal head weighting has functionally or completely corrected cervical lordosis, a patient's spine will accept lateral head weighting and a lateral spine adjusting forces. Lateral head weighing procedures can identify lateral joint and ligament instability and can be used to correct lateral cervical and lateral upper thoracic subluxation complexes and scoliosis.

Figure 10:
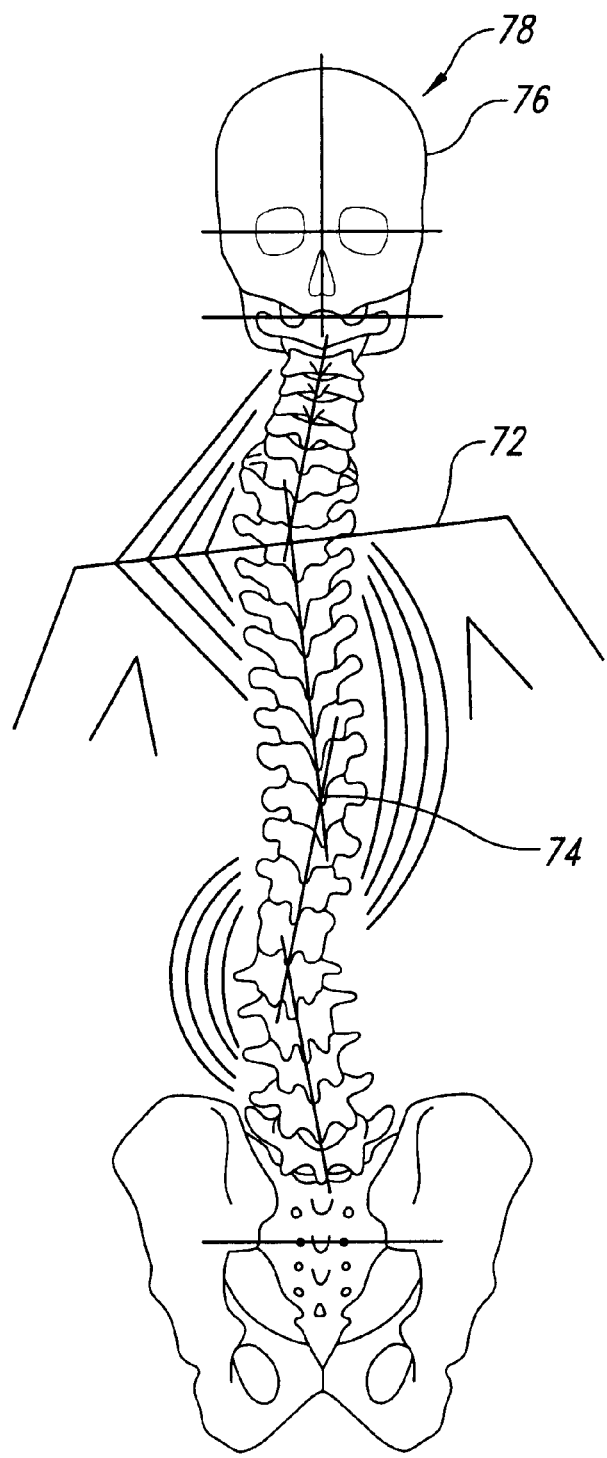
FIG. 10 is an illustration of an abnormal shoulder condition caused by subluxation of the spine.

For example, a patient's high shoulder 72, as illustrated in FIG. 10, is associated with a lateral acute angel deviation to the high shoulder side, which forms the lower cervical and upper dorsal spine (C-D) angle 74 on that side. Therefore, the high shoulder side 76 of the head 78 is usually weighted to aid lateral spine correction down to the T7 vertebrae. However, during trauma, the spinal ligaments that hold the vertebrae together and act as the fulcrums for the spinal motion muscles to act upon are often injured. Such injured ligaments cannot be identified under normal motion or static A-P x-ray examination.

A spine with injured ligaments will not act and react as does a non-injured spine. Rather, they react opposition to what is expected when subjected to external weight or mechanical forces. X-rays of the laterally-loaded head easily identify injured ligaments of the lateral cervical and thoracic spine down to the T7 vertebrae, and they help the clinician to accurately determine the patient's injuries and treatment needs, including the following:

(a) Injury of lateral cervical-dorsal joints and ligaments.

(b) When ligaments are injured, this examination insures that proper correcting procedures are used so that the injured spine is not allowed to heal in subluxated positions that produce abnormal form, function, and pain.

(c) They determine which side of the head should be weighted when ligaments heal in order to exercise, strengthen, and balance the involved muscles without further injuring the patient.

(d) The amount of weight that is required or that will ultimately be necessary to correct and maintain the A-P cervical-upper thoracic spine can be determined.

(e) Non-compensated and uncompensated spinal configurations of the ligament-injured spine are identified by the loaded x-rays examination so that special treatment procedures can be devised and implemented.

(f) Phasic muscles fibers are changed to postural muscles fibers on the convex side and atrophy on the acute angle side of the various subluxation angles by the body as needed to stabilize the injured spine. However, this stabilization reduces spinal function. Therefore, this important evaluation examination identifies the muscles in need of equalizing and strengthening the rehabilitation procedures so that spinal correction and maintenance can become a reality.

In accordance with one embodiment of the present invention, the following procedure can be used to identify the side of the head and the amount of head weighting to be used.

Figure 11:
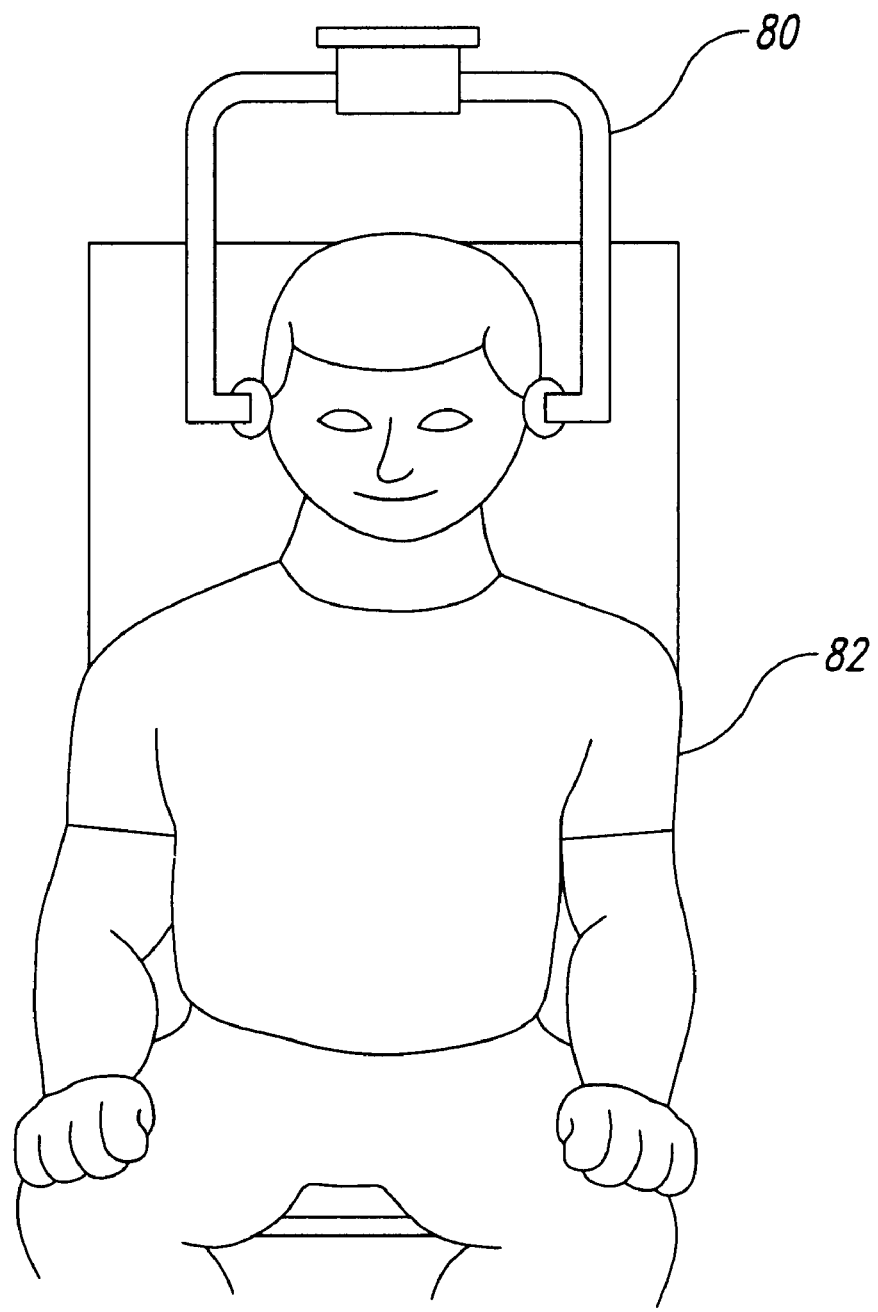
FIG. 11 illustrates the use of self-centering head clamps prior to x-ray of a patient.

Firstly, an A-P skull-cervical-upper-thoracic x-ray image is obtained, preferably by taking an x-ray on a 14×17 or larger film. To insure the x-ray is not distorted, a self-centering head clamp 80 should be used after the patient's skull 82 is aligned in the posture they are presented with, as shown in FIG. 11.

Figure 12:
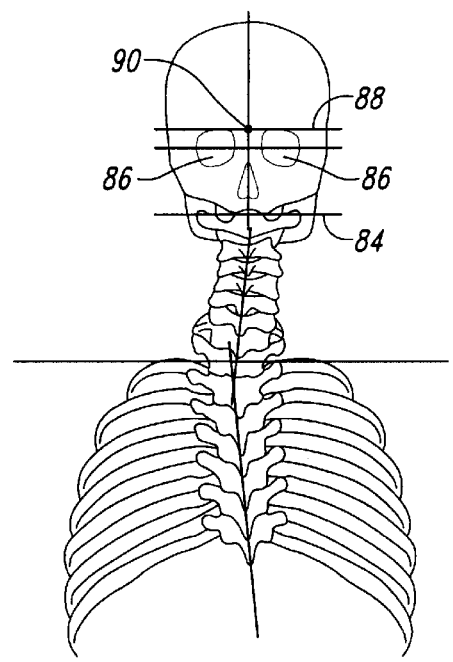
FIG. 12 is an illustration of the skull, spine, and ribcage showing drawn lines to establish the center of skull mass.

Secondly, once the x-ray image is obtained, a line 84 should be drawn between the outer canthus of the two eye orbits 86. This line should be parallel to the top 88 of the eye orbits 86. The line 84 just drawn should be bisected in order to establish the center 90 of skull mass in the A-P dimension as shown in FIG. 12.

Figure 13:
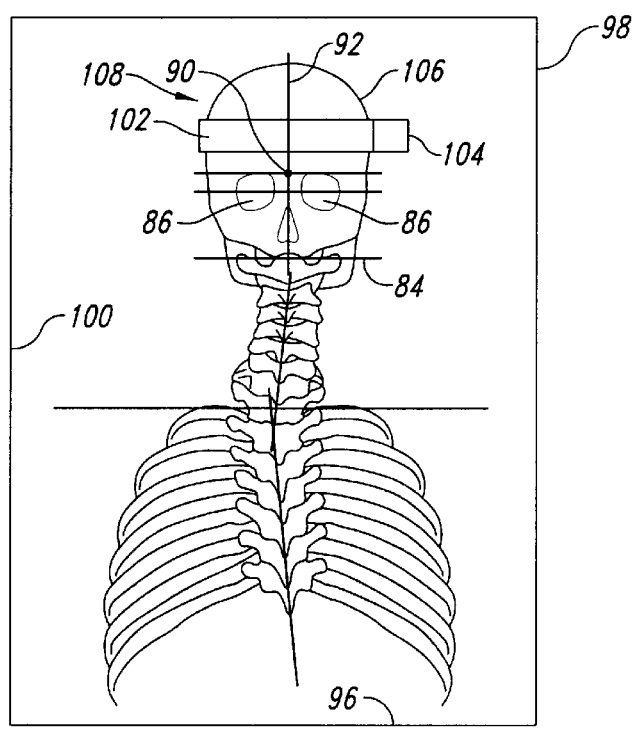
FIG. 13 is an illustration of the placement of a headband formed in accordance with the present invention on the skull depicted in FIG. 12.

Thirdly, as shown in FIG. 13, a line 92 should be erected from the center 90 of the skull 94 mass and perpendicular to the eye line. That line 92 should extend perpendicular to the bottom 96 of the film 98, as in drawing a gravity line. This line 92 should be parallel or nearly parallel to the side 100 of the film as shown in FIG. 13.

Figure 14:
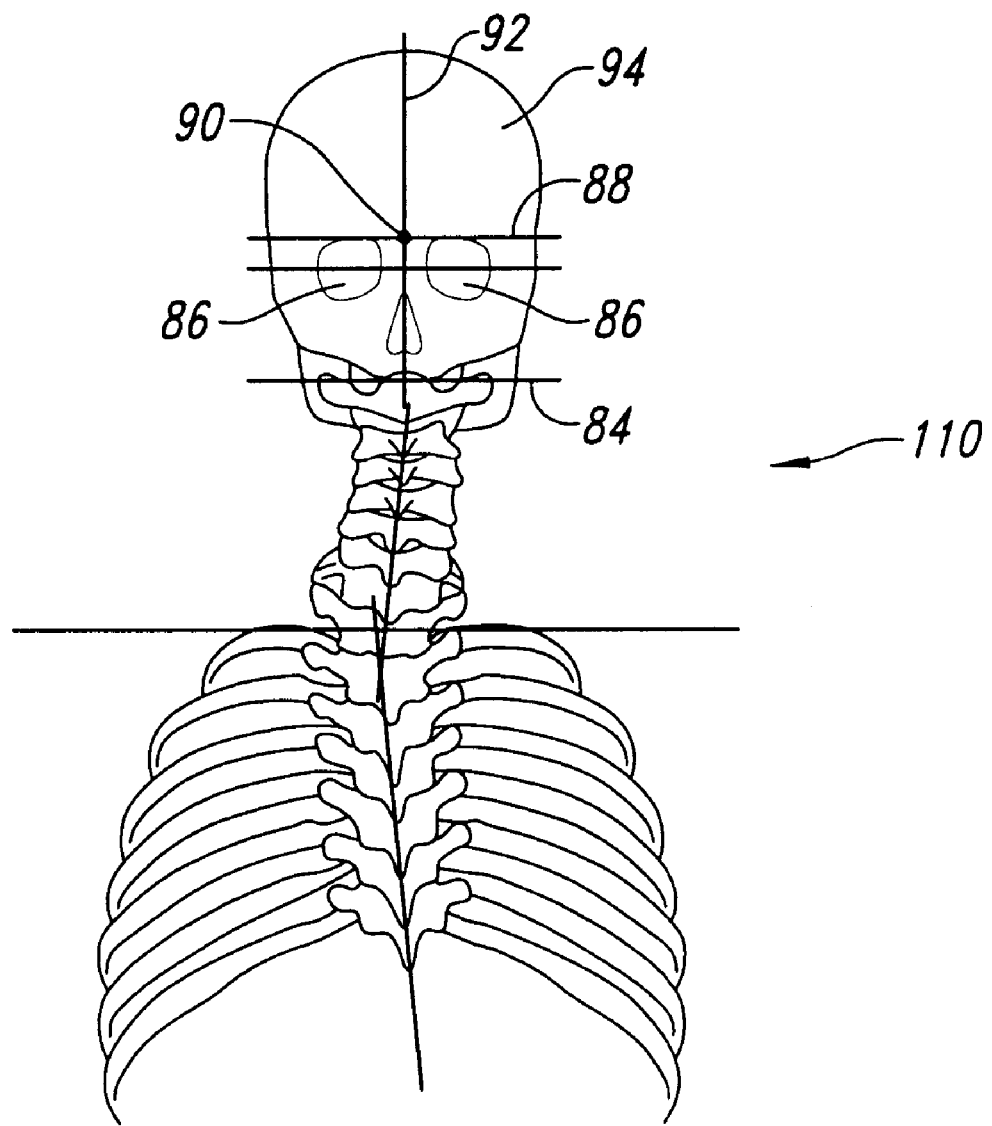
FIG. 14 is an illustration of the skull, spine, and ribcage of FIG. 13 with the head weighted in accordance with the present invention and the gravity line and upper thoracic spine center moved closer together.

Fourthly, a headband 102 weighted with four to six pounds of weight 104 should be placed on the patient's high-shoulder side 106 of the head 108 and a further x-ray image 110 of the A-P full spine or skull-cervical-upper thoracic region should be taken. Subsequently, the further x-ray image 110 should be marked as described above. The patient's gravity line and upper thoracic spine center line 92 should be closer together in the weighted x-ray image 110 than in the non-weighted x-ray 98, as shown in FIG. 14 when compared with FIG. 13. If the gravity line in the weighted x-ray image 110 is further from the thoracic spine center than it is in the non-weighted x-ray image 98, this is indicative of ligament damage. Normally, rehabilitation and spinal correction procedures will not work as expected on this patient.

When the foregoing x-ray evaluation indicates ligament damage, the weight should be moved to the opposite side of the head and the foregoing repeated until a final weighting is obtained.

The side of the head that the weight should be used on when starting rehab-corrective care will cause the gravity line and the spine line to move closer together while causing the A-P spine to straighten. The weight of the opposite side of the head reverses the process. Additional weight will be needed when the original weight used during the evaluation x-rays caused the gravity line to move toward but not completely to the center of the thoracic spine.

Additional weight can be calculated using the following procedure:

(a) Determine the amount of correction the original weight produced. For example, if the original weight was six pounds and it produced 75% correction, then the addition of 25% more weight should cause the gravity line to completely align with the center of the thoracic spine.

(b) The foregoing should be verified by retaking an remeasuring the x-ray image as described above.

(c) The evaluation should continue with repeating the foregoing process until the ultimate amount of weight necessary is determined.

When too much weight is applied to the side of the head in the weighted evaluation process, the gravity line and thoracic spine may not correct further, and may possibly move further apart. Therefore, the weight should be reduced back to the original amount. The reduced amount of weight should be used for two-six weeks to allow the muscles to strengthen, then the additional amount of weight calculated should be applied. Reevaluation and additional weight should be done as needed.

Another embodiment of the method of lateral head weighting in accordance with the procedure of the present invention will now be described in conjunction with FIGS. 15–19. In accordance with the method of the present invention, lateral head weighting begins slowly and deliberately. Referring to FIGS. 16a–b, a frontal head weight 112 is placed on the head 114 of the patient 116 with a removable weight holder 118. The weight 112 is positioned over the high shoulder side 120 in patients with a number 1 posture, i.e., head level and shoulder 120 high. Similarly, the weight 112 is placed on the same side of the head in posture number 2, shown in FIG. 15b, where the shoulders are level and the eyes are tilted, with the weight on the side the head is tipped toward, i.e., the side where the eyes 122 are tilted.

In posture 3, shown in FIG. 16a, the eyes 122 and the shoulder 120 are level, but the head 114 is shifted laterally. In this case, the weight 112 is placed on the side that the head 114 is shifted away from. The opposite head lateral shift is shown in posture number 4 in FIG. 16b.

It should be noted that in lateral head shifting, shown in postures 3 and 4 in FIGS. 16a–b, this is indicative of ligament injury. Therefore, these patients must be weighted on the opposite side of the head initially and then special exercises should be required, as discussed further below. It should further be noted that the spine is three dimensional. Therefore, rapid lateral shifting of the frontal weight to the side may actually decrease previously-corrected cervical lordosis.

Figure 17:
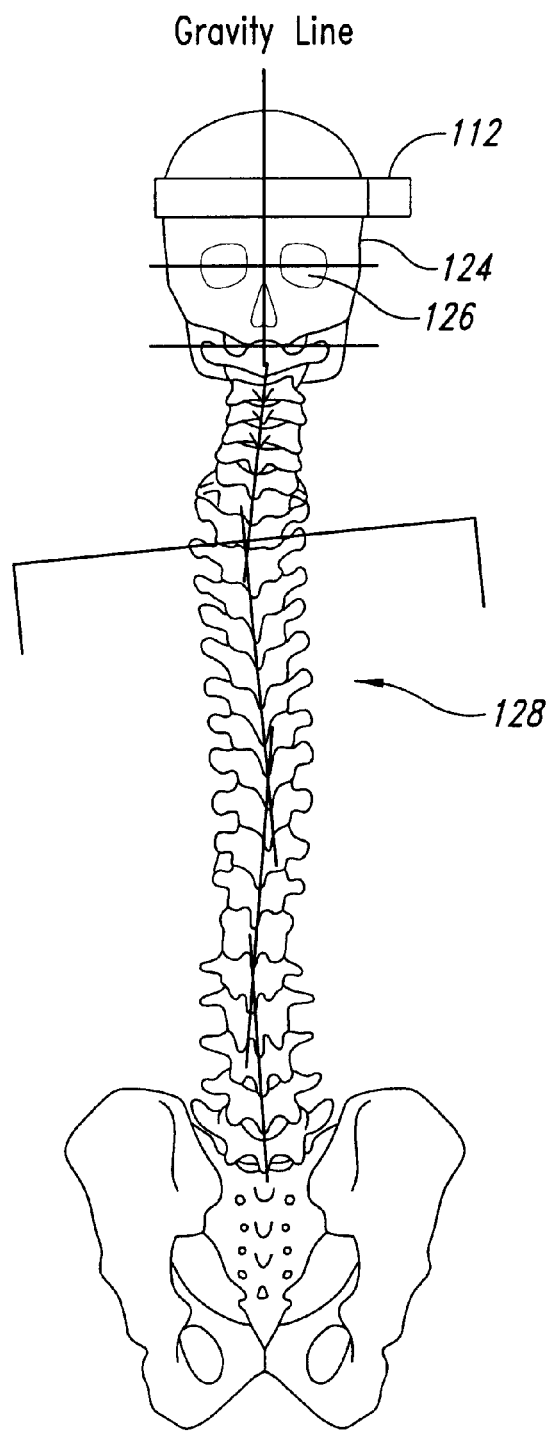
FIG. 17 is a frontal view of the spine showing over-contraction of the neck and upper body muscles.
Figure 18:
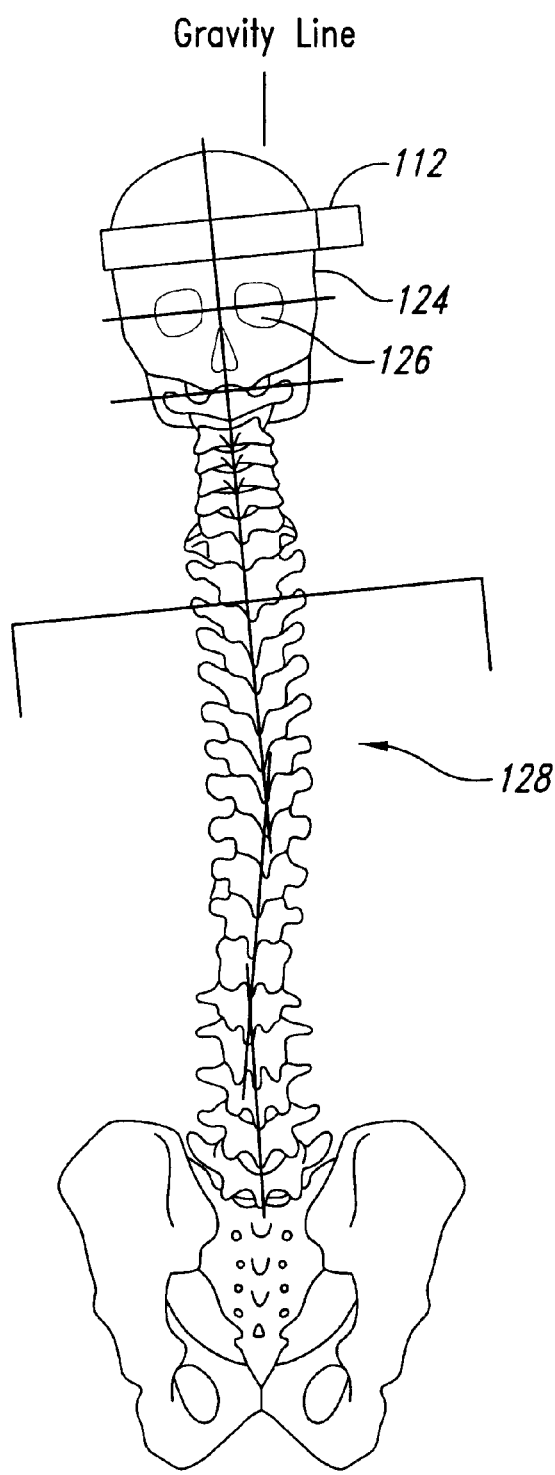
FIG. 18 is a frontal view of the spine of FIG. 17 showing the head over to the side of the over-contractions.
Figure 19:
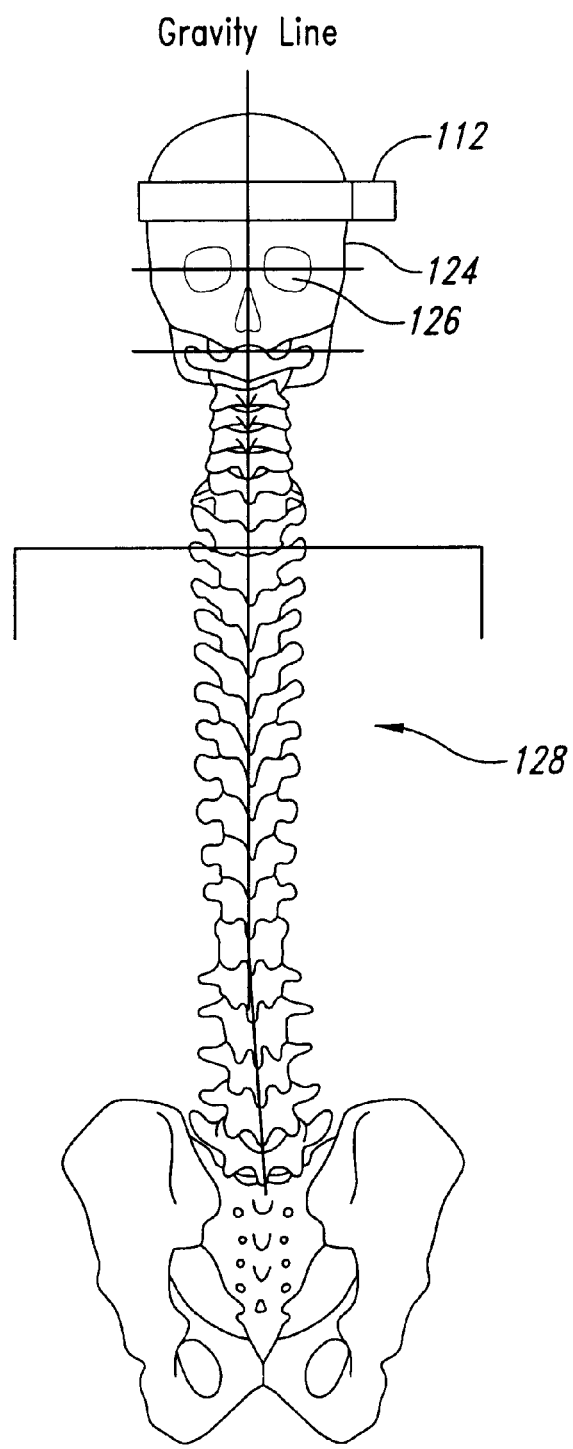
FIG. 19 is a frontal view of the spine in alignment using the lateral head weighting procedures of the present invention.
Figure 20:
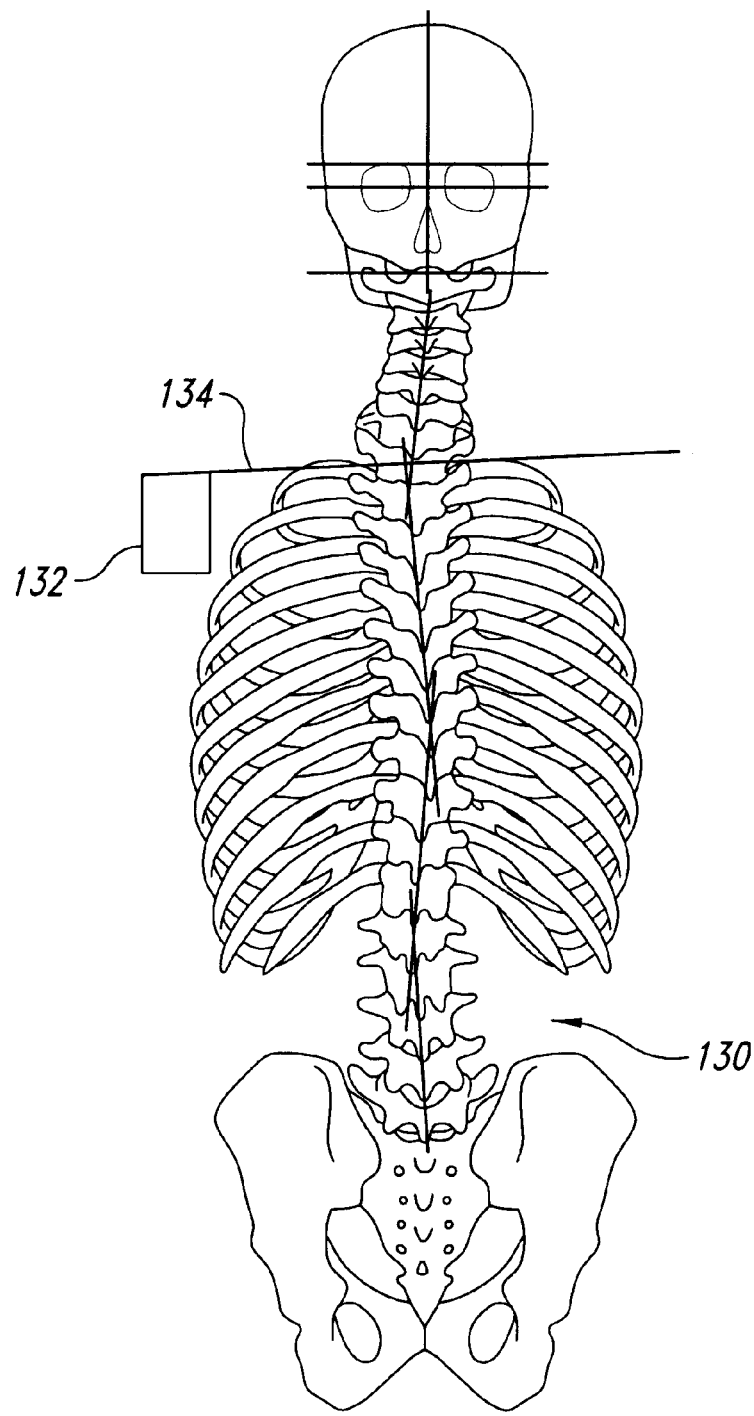
FIG. 20 is an illustration of an A-P full spine x-ray with a lowered shoulder weighted in accordance with the present invention.

Lateral head weighting causes a reflex over-contraction of the patient's neck and upper body muscles on the side opposite the weight, as shown in FIG. 17. The overcontracted muscles tend to pull the head 124 and eyes 126 to the side of the overcontractions, as shown in FIG. 18. This new lateral position of the head and eyes then activates the person's righting reflexes, which repositions and corrects the head and upper spine 128 to be in alignment with gravity down to the T7 vertebrae, as shown in FIG. 19.

Ideally, head weighting should begin within at least forty seconds after rising in the morning. In one embodiment, head weighting could be used in combination with cervical traction, i.e., within forty seconds after completing cervical traction or within forty seconds after being adjusted by a practitioner. Head weighting may cause nausea if used later in the day without first being used in the morning as directed.

In the event too much weight is used or the head weight is left on too long, the patient's head will tip toward the weight. To correct this, the amount of weight should be reduced until this head tipping no longer happens and the weight is easily tolerated.

It should be noted that during the rehabilitation process, the muscles on the exercised side over-strengthen, thereby making it necessary to change the position of the weight. As the need arises, the patient should be re-x-rayed starting with four to six pounds on the opposite side of where they previously had the weight.

Furthermore, if shoulder weighting in used in conjunction with hip weighting (described below), then a change in head weighting may also require a change in the weighting of the hip.

In instances where lateral head weighting identifies ligament instability, the clinician should determine beneficial muscle exercises that will stabilize the spine while the ligaments are healing. Corrective exercises are utilized after stability is achieved.

The system of the present invention also includes lateral shoulder weighting and related evaluation. Lateral shoulder weighting by itself has little effect on the upper thoracic spine (above the T7 vertebrae); however, it has its greatest effect in the correction of the lower thoracic (below the T7 vertebrae) and the upper lumbar spine above the L3 vertebrae.

It should be noted that shoulder and hip weighting (described below) are performed later and in addition to forward and lateral head weighting. Hip weighting is most effective after head and shoulder weighting has produced its maximum results in the lateral and A-P spine.

The lateral shoulder weighting and evaluation procedures will now be described in conjunction with FIGS. 16 and 17.

Figure 15A:
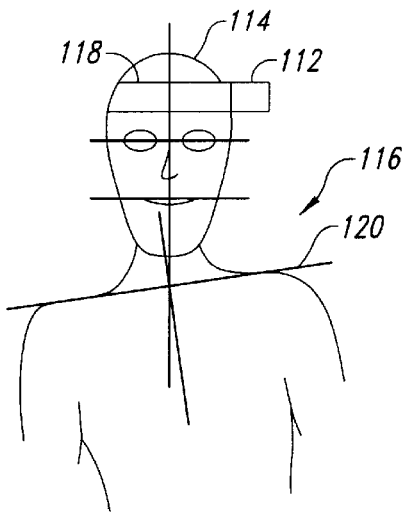
FIGS. 15a–b are front views of level head posture and level shoulder posture, respectively.
Figure 15B:
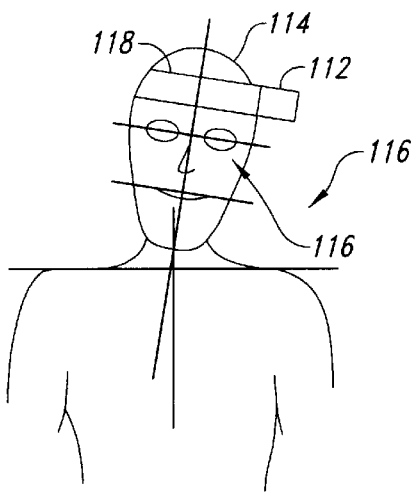
Figure 16A:
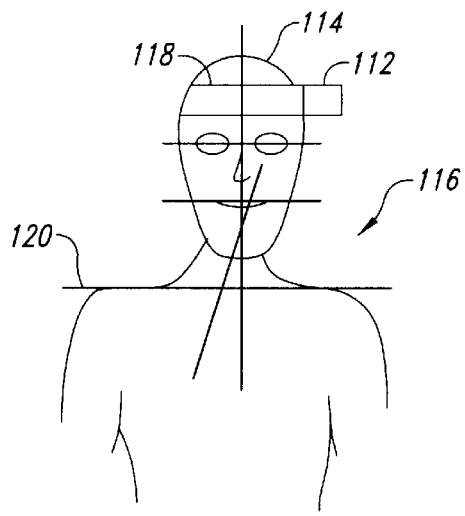
FIGS. 16a–b are frontal views of alternate head weighting in accordance with the method of the present invention.
Figure 16B:
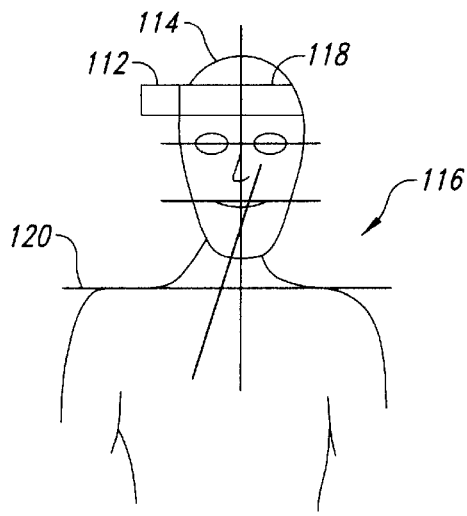

First, the A-P full spine are sectional films used above in conjunction with the lateral head weighting can be used to determine if the spine 130 is compensated, as shown in FIG. 15a. If the spine 130 is compensated, approximately eight pounds or more of weight 132 (up to 50 pounds) should be placed on the outside of the low shoulder 134 and another x-ray taken.

Figure 21:
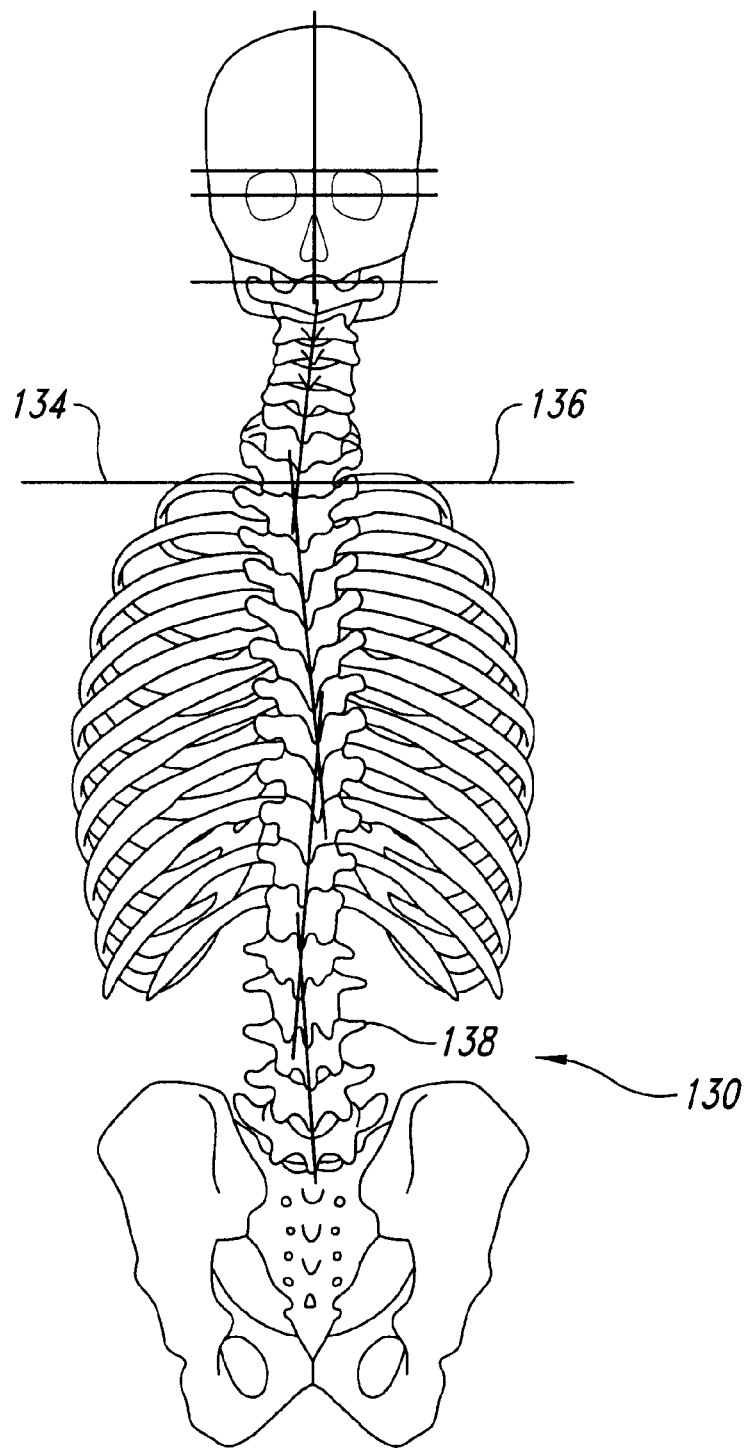
FIG. 21 is an illustration of the full spine of FIG. 15 corrected in accordance with the present invention.

The patient's righting reflexes should lift the low shoulder 134 as high or higher than the opposite shoulder 136, with a corrective change in the lower thoracic, upper lumbar spine 138 if the ligaments are intact and sufficient weight was used to activate the patient's righting reflexes without overloading the muscles, as shown in FIG. 21. This action should cause a correction of the lower thoracic spine 138. In the event that the weighting of the low shoulder 134 causes the lower dorsal spine to further misalign with the upper thoracic spine or the lumbar spine 138, ligament instability is indicated in this area. To verify these findings, the same weight 132 should be placed on the opposite shoulder 136 and a further x-ray image obtained and evaluated. Such evaluation will enable the clinician to make a rational decision on how to proceed with muscle rehabilitation and adjusting the needs of the patient.

In the event the opposite (high) shoulder 136 needs weighting, the clinician should determine muscle exercises that will help stabilize the spine while it is healing, as well as maintenance exercises after it has healed.

For patients that have loss of lumbar lordosis with forward protruding hip posture and lateral spine deviations, it is noted that lateral-posterior shoulder weighting has a profound effect on correcting posture, scoliosis, and loss of lumbar lordosis, as well as the lumbo-dorsal spine subluxations. The following procedures should be used:

First, when combined posture subluxation is evident, the lateral shoulder weight 132 should be placed on the patient's back as well as on the shoulder. Furthermore, the amount of weight is usually much greater, starting for example with up to twenty-five pounds and additional weight added as needed. At times, one hundred or more pounds of weight have been required.

Usually the patient's spine is not in compensation; therefore, it is a clinical decision as to which side to weight first during the x-ray examination. By a process of elimination, the clinician will be able to determine which shoulder needs weighting as well as the amount of weight required.

Figure 22:
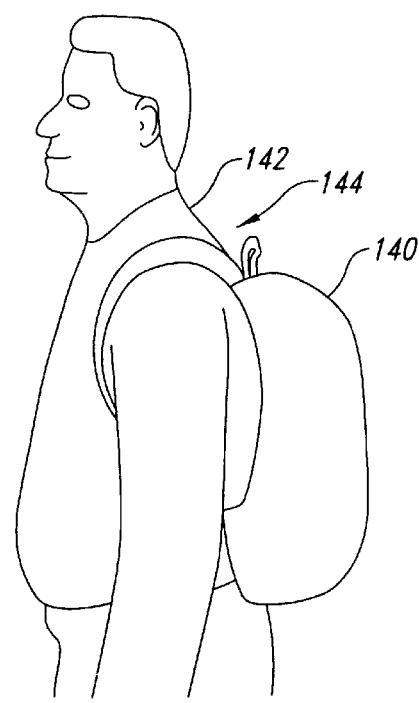
FIG. 22 is a side view of a weighted pack on the low shoulder side of a patient's back.

The best method to determine the side and need of weighting and the amount of weight required is to load one side of a backpack 140 with twenty-five pounds of weight and the other side with foam rubber. The weighted side should be placed on the low shoulder side 142 of the back 144, as shown in FIG. 22. The weighted backpack 140 should cause the hips to move back at least partially under the weight.

Should the initial weight not completely cause the affected hip to move under the weight, more weight should be added until the correction is achieved or until the patient's posture is negatively affected. If the hips have not been corrected relative to the upper body, the weight in the pack 140 should be shifted to the other shoulder and a visual determination made as to which side caused the greatest lateral spine shift without compromising the hips and upper back correction.

An A-P x-ray of the spine should now be taken in order to confirm the visual examination findings. In the event the x-ray image give evidence that is contrary to visual observations, the x-ray image findings should take precedence over the visual examination.

It should be noted that this type of subluxation complex always has involved the muscles. The clinician should identify the involved muscles and devise rehabilitation exercises for them. In addition, front, lateral, or front-lateral combined head weighting is always used when utilizing the shoulder and hip weighting.

Figure 23:
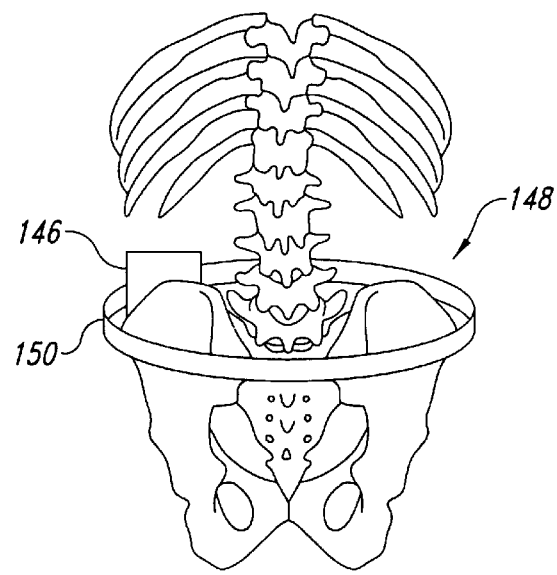
FIG. 23 is an illustration of the spine and pelvic bones weighted in accordance with the present invention.

Referring next to FIG. 23, shown therein is a hip weight 146 that is placed on the front and side of a hip 148 that appears to be rotated forward. This is generally the preferred placement of external hip weights using an externally removable weight strap 150 or belt. Typically, this is usually the hip 148 on the measured acute lumbo-sacral angle on an A-P x-ray as shown in FIG. 23.

Hip weighting usually starts with an initial weight of eight to ten pounds, and more weight is added if needed. A reevaluation is performed by taking an additional x-ray after the initial weight is placed on the hip. If the hip weight appears to cause the hip rotation to worsen, the hip weight should be placed on the opposite hip and reevaluated. Once the clinician has determine the best weight and placement, a weighted x-ray of the lower spine is retaken.

X-ray evaluation may also determine which hip is in need of weighting. X-ray evaluation takes precedence over visual evaluation.

Special head weighting exercises can be performed to correct uncorrected spinal rotation and uncorrected lateral deviation subluxations. Often, rotations of the skull-atlas and the axis spinous do not align or function as expected. Typically this is because of unresolved injury that has caused a ligament, such the alar ligament to tear or it involves loss of disc height or joint pathology, or combinations of two or more of the foregoing. Routine examinations do not detect lateral spine deviation injuries, and therefore they are not corrected with routine spinal care. These unresolved problems require special care.

In accordance with another embodiment of the present invention, special head weighting exercises are effective for correcting unresolved problems caused by torn ligaments. To perform these special exercises, the following should be done:

(a) A special headband should be fitted on the head of the user and weighted with six to fifteen pounds of weight on the forehead.

(b) An attempt should be made to exercise the neck through its full range of motion, identifying any restricted mobility. The patient should then bend over and place the hands on the knees and repeat the exercise, especially in the identified areas of restriction. The head should be extended and the user should work up to twenty extension head lifts.

(c) Next, the weight is shifted to the side of the head and the exercises are repeated. The weight should then be shifted to the other side of the head and the exercises again repeated.

(d) Exercise effects should be noted in the neck, chest, and back down to the T7 vertebrae.

Figure 24:
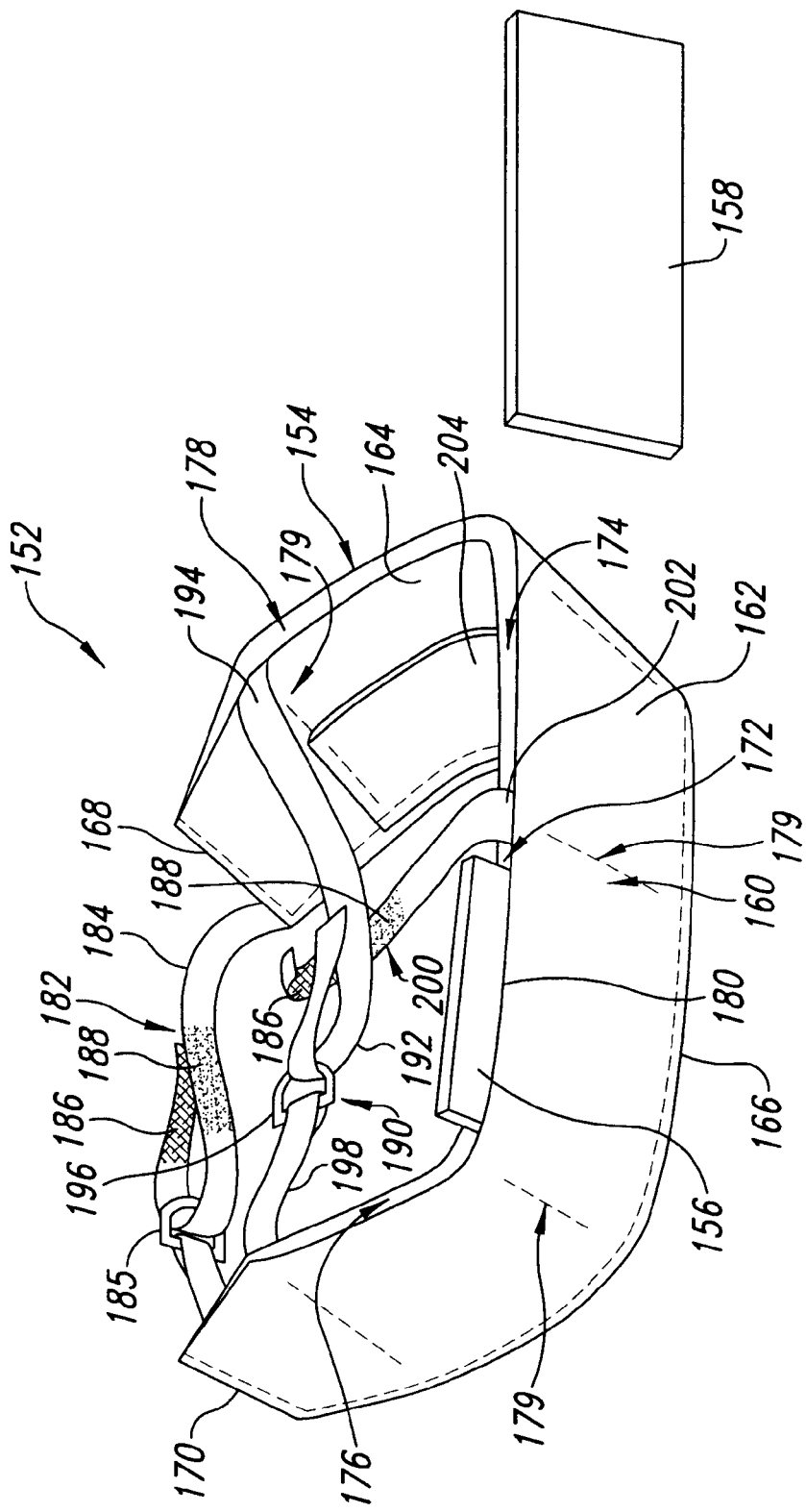
FIG. 24 is an isometric projection of a head weighting system formed in accordance with the present invention.

FIG. 24 illustrates a head weighting system 152 formed in accordance with another embodiment of the invention. This system 152 includes a headpiece 154 and a plurality of weights 156 and 158.

The headpiece 154 is formed to fit over a patient's head and support one or more of the weights 156, 158 in a weight holder 160. The weight holder 160 is formed from a first wall 162 and a second wall 164 of material that are stitched together along the length of a bottom side 166 and the length of a first and second end 168, 170, respectively. The material may be formed from cloth, flexible plastic, or other materials that provide sufficient strength and rigidity to hold the weights to the patient's head.

A pair of front pockets 172, 174, and a pair of side pockets 176, 178, are formed by stitching 179 between the bottom side 166 and a top side 180 of the headpiece 154. Ideally, the stitching need not extend the full distance between the top and bottom sides 180, 166. Preferably, the front and side pockets 172, 174, 176, 178, are sized and shaped to receive one, and preferably two, of the weights 156, 158 in each pocket.

An adjustable strap 182 is attached at each end 168, 170 of the headpiece 154 to hold the headpiece 154 on a user's head. In this embodiment, the adjustable strap 182 includes a first strap member 184 attached to the first end 168 and a rigid ring member 184 attached to the second end 170. The first strap member 184 is sized and shaped to loop through the rigid ring member 184 and attach back on itself, ideally with hook and loop fasteners 186, 188. It is to be understood that other adjustment systems may be used as known to those skilled in the art for holding the headpiece 154 to a user's head.

To aid in holding the headpiece 154 to a patient's head, a second adjustable strap 190 is attached across the top side 180 of the headpiece 154. The second adjustable strap 190 is formed from a first strap member 192 having one end 194 attached to existing pocket stitching 179 adjacent the first end 168 and a rigid ring member 196 attached by a short tab 198 adjacent the second end 170. The second adjustable strap 190 is configured in the same manner as the first adjustable strap 182 and will not be described in further detail herein. Because of the substantial amount of weight held by the headpiece 154, which can cause the headpiece 154 to slip down on a patient's forehead, the second adjustable strap 190 is designed to maintain the headpiece 154 in a desired position on the patient's head.

To further distribute the load and increase the patient's comfort, as well as maintain the headpiece 154 in position, a third adjustable strap 200 is provided having one end 202 attached to existing stitching 179 between the front pockets 172, 174. The third adjustable strap 200 is sized and shaped to loop around the second adjustable strap 190 and attach to itself in the same manner as the first and second adjustable straps 182, 190.

To further improve comfort for the user, padding 204 is attached by the existing stitching 179 to the second wall 164 to bear against the patient's head.

The head weighting system 152 is to be used under the direction of a skilled medical professional. The appropriate amount of weight is applied to a patient's head by inserting one or more of the plurality of weights 156, 158 into the headpiece 154 by inserting the weights 156, 158 into the pocket 172, 174, 176, 178, as directed by the medical professional. Prior to placing the weights in the headpiece 154, the adjustable straps 182, 190, 200 should be adjusted to fit the patient's head. After the system 152 is placed on the patient's head, the straps can be further adjusted as necessary for support and comfort. Weights can be interchanged when the system 152 is on the patient's head as desired.

While various embodiments of the invention have been illustrated and described, various changes may be made therein without departing from the spirit and scope of the invention. Consequently, the invention is to be limited only by the scope of the claims that follow and the equivalents thereof.

The embodiments of the invention in which an exclusive property or privilege is claimed are defined as follows:

1. A method for spinal examination and treatment, comprising:
   obtaining a first image of a patient's spine and head;
   determining the location of the center of the patient's head relative to the anterior one-third of the C4/C5 disc;
   weighting the front of the patient's head; and
   obtaining a further image of the patient's spine and head, redetermining the location of the center of the patient's head relative to the anterior one-third of the C4/C5 disc, and adjusting the weight on the front of the patient's head repeatedly until a final weighting is reached where the center of the patient's head is substantially aligned over the anterior one-third of the C4/C5 disc.

2. The method of claim 1, further comprising weighting the patient's head with the final weight daily for a predetermined period of time.

3. The method of claim 2, wherein weighting the patient's head comprises maintaining the patient's head in an upright position when weighted.

4. The method of claim 2, wherein the predetermined period of time comprises about twenty minutes.

5. The method of claim 4, wherein the patient's head is weighted with the final weight at least two to three times daily for the predetermined period of time.

6. The method of claim 2, wherein weighting the patient's head comprises attaching a removable external weight on the front of the patient's head.

7. The method of claim 2, wherein obtaining a first image and obtaining further images comprises obtaining neutral lateral cervical X-ray images.

8. A method for spinal examination and treatment, comprising:
   obtaining a first image of a patient's spine and head;
   measuring a lateral distance between the center of the head and the front of the C4/C5 disc;
   measuring the lordotic curvature of the spine;
   weighting the patient's head in an upright position;
   obtaining further images of the patient's spine and head, remeasuring the lateral distance and the lordotic curvature, and adjusting the weighting of the patient's head repeatedly to obtain a final weight where the lateral distance between the center of the patient's head and the front of the C4/C5 disc is within a predetermined range.

9. The method of claim 8, further comprising weighting the patient's head with a final weight daily for a predetermined period of time.

10. The method of claim 9, further comprising weighting the patient's head at least two to three times daily for the predetermined period of time.

11. The method of claim 10, wherein weighting the patient's head comprises weighting the patient's head immediately after arising in the morning.

12. The method of claim 8, wherein weighting the patient's head comprises attaching a weight to the front of the patient's head with an external removable weight holder.

13. The method of claim 12, wherein measuring the lordotic curvature comprises erecting a Jackson's stress line on the back of the C2 and the C7 vertebrae and extending the lines until they intersect;
   measuring the acute angle wherein the C2 and the C7 Jackson's stress lines intersect.

14. The method of claim 8, wherein obtaining a first image and obtaining further images comprises obtaining A-P skull-cervical-upper-thoracic X-ray images.

15. A method for spinal examination and treatment, comprising:
   obtaining a first image of a patient's spine;
   determining if the spine is compensated by a low shoulder;
   weighting the low shoulder of the patient;
   obtaining further images of the patient's spine, determining spinal compensation, and adjusting the weighting of the patient's shoulder repeated until a final weighting is reached where the spine is substantially in alignment with itself.

16. The method of claim 15, wherein determining if the spine is compensated by a low shoulder comprises examining the first image of the patient's spine.

17. The method of claim 15, wherein weighting the low shoulder comprises attaching a weight to the low shoulder with an external adjustable weight holder, and further adjusting the weighting comprises adjusting the position and the amount of weight on the patient's low shoulder.

18. The method of claim 15, wherein obtaining a first image and obtaining further images comprises obtaining A-P full spine X-ray images.

19. A method for spinal examination and treatment, comprising:
   obtaining a first image of a patient's pelvic and lower lumbar area;
   determining if the patient's hip is rotated forward;
   weighting the patient's hip; and
   obtaining further images of the patient's pelvic and lower lumbar area, redetermining if the patient's hip is rotated forward and adjusting the weighting on the patient's hip until a final weighting is reached where the hip is no longer rotated forward.

20. The method of claim 19, wherein weighting the patient's hip comprises removably attaching an external weight to a location on the patient's hip that is rotated forward, and further wherein adjusting the weighting comprises adjusting one or more of the locations and amount of weight.

21. The method of claim 19, wherein obtaining a first image and obtaining further images comprises obtaining X-ray images of the patient's pelvic and lower lumbar area.

22. The method of claim 19, further comprising weighting the patient's hip that is rotated forward with a removable external weight daily for a predetermined period of time.

23. A method for examining and treating a patient's skeletal system, comprising:
   obtaining a first image of one or more areas of a patient's skeletal system;

determining areas of abnormal condition of the patient's skeletal system;

weighting the patient's skeletal system to correct the areas of abnormal condition; and obtaining further images of the patient's skeletal system, redetermining the presence of areas of abnormal condition of the patient's skeletal system, and adjusting the weighting of the patient's skeletal system until a final weighting is reached where the patient's areas of abnormal condition of the skeletal system are no longer abnormal.

24. The method of claim 23, wherein weighting the patient's skeletal system comprises attaching at least one weight externally to the patient's body with at least one removable external weight holder.

25. The method of claim 24, further comprising weighting the patient's skeletal system with the final weight daily for a predetermined period of time.

26. The method of claim 24, wherein determining areas of abnormal condition of the patient's skeletal system comprises measuring the first image to determine skeletal misalignment.

27. The method of claim 24, wherein adjusting the weighting comprises adjusting one or more of the position and the amount of the weight.

28. The method of claim 24, wherein obtaining a first image and obtaining further images comprises obtaining X-ray images.

* * * * *